United States Patent
Escano et al.

(10) Patent No.: US 7,591,843 B1
(45) Date of Patent: Sep. 22, 2009

(54) DELIVERY SYSTEM FOR MODULAR ENDOGRAFT WITH SUPERIOR ATTACHMENT SYSTEM

(75) Inventors: Arnold M. Escano, Santa Clara, CA (US); Patrick J. Massetti, San Mateo, CA (US); Shuji Uemura, San Francisco, CA (US); Michael F. Wei, San Mateo, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 1204 days.

(21) Appl. No.: 10/650,477

(22) Filed: Aug. 28, 2003

Related U.S. Application Data

(63) Continuation-in-part of application No. 10/222,728, filed on Aug. 16, 2002.

(51) Int. Cl.
A61F 2/06 (2006.01)
A61F 11/00 (2006.01)

(52) U.S. Cl. ............................ 623/1.11; 606/108

(58) Field of Classification Search ............ 623/1.11, 623/1.12; 606/191, 194, 195, 198, 108
See application file for complete search history.

(56) References Cited

U.S. PATENT DOCUMENTS

| | | | |
|---|---|---|---|
| 5,035,706 A | 7/1991 | Gianturco | |
| 5,064,435 A | 11/1991 | Porter | |
| 5,354,309 A | 10/1994 | Schnepp-Pesch et al. | |
| 5,387,235 A | 2/1995 | Chuter | |
| 5,507,771 A | 4/1996 | Gianturco | |
| 5,562,724 A | 10/1996 | Vorwerk et al. | |
| 5,575,817 A | 11/1996 | Martin | |
| 5,628,788 A | 5/1997 | Pinchuk | |
| 5,632,772 A | 5/1997 | Alcime et al. | |
| 5,639,278 A | 6/1997 | Dereume et al. | |
| 5,643,312 A | 7/1997 | Fischell et al. | |
| 5,653,743 A | 8/1997 | Martin | |
| 5,676,696 A | 10/1997 | Marcade | |
| 5,683,449 A | 11/1997 | Marcade | |
| 5,683,450 A | 11/1997 | Goicoechea et al. | |
| 5,713,917 A | 2/1998 | Leonhardt et al. | |
| 5,716,365 A | 2/1998 | Goicoechea et al. | |
| 5,718,724 A | 2/1998 | Goicoechea et al. | |
| 5,723,004 A | 3/1998 | Dereume et al. | |

(Continued)

FOREIGN PATENT DOCUMENTS

WO 84/02266 6/1984

(Continued)

OTHER PUBLICATIONS

Chuter, et al., "Transfemoral Endovascular Aortic Graft Placement," Journal of Vascular Surgery, vol. 18, No. 2, Aug. 1993, pp. 185-197.

(Continued)

*Primary Examiner*—Vy Q Bui
(74) *Attorney, Agent, or Firm*—Brooks, Cameron & Huebsch, PLLC

(57) ABSTRACT

The present invention embodies delivery systems and methods of repairing vasculature. Various embodiments of bifurcated grafts and limb components can be delivered by delivery systems that provide enhanced control of self-expanding structure of a modular grafting system.

26 Claims, 11 Drawing Sheets

U.S. PATENT DOCUMENTS

| | | | |
|---|---|---|---|
| 5,728,131 | A | 3/1998 | Frantzen et al. |
| 5,741,325 | A | 4/1998 | Chaikof et al. |
| 5,755,769 | A | 5/1998 | Richard et al. |
| 5,769,887 | A | 6/1998 | Brown et al. |
| 5,776,180 | A | 7/1998 | Goicoechea et al. |
| 5,782,904 | A | 7/1998 | White et al. |
| 5,800,508 | A | 9/1998 | Goicoechea et al. |
| 5,824,034 | A | 10/1998 | Schmitt et al. |
| 5,824,037 | A | 10/1998 | Fogarty et al. |
| 5,824,042 | A | 10/1998 | Lombardi et al. |
| 5,851,228 | A | 12/1998 | Pinheiro |
| 5,855,598 | A | 1/1999 | Pinchuk |
| 5,916,263 | A | 6/1999 | Goicoechea et al. |
| 5,938,696 | A | 8/1999 | Goicoechea et al. |
| 5,948,017 | A | 9/1999 | Taheri |
| 5,993,481 | A | 11/1999 | Marcade et al. |
| 6,015,431 | A | 1/2000 | Thornton et al. |
| 6,051,020 | A | 4/2000 | Goicoechea et al. |
| 6,077,297 | A | 6/2000 | Robinson et al. |
| 6,099,558 | A | 8/2000 | White et al. |
| 6,102,938 | A | 8/2000 | Evans et al. |
| 6,102,940 | A | 8/2000 | Robichon et al. |
| 6,110,198 | A | 8/2000 | Fogarty et al. |
| 6,117,167 | A | 9/2000 | Goicoechea et al. |
| 6,123,722 | A | 9/2000 | Fogarty et al. |
| 6,149,682 | A | 11/2000 | Frid |
| 6,152,956 | A | 11/2000 | Pierce |
| 6,221,102 | B1 | 4/2001 | Baker et al. |
| 6,241,759 | B1 | 6/2001 | Piplani et al. |
| 6,361,556 | B1 | 3/2002 | Chuter |
| 6,592,615 | B1 | 7/2003 | Marcade et al. |
| 6,761,733 | B2 * | 7/2004 | Chobotov et al. .......... 623/1.12 |

FOREIGN PATENT DOCUMENTS

| | | |
|---|---|---|
| WO | WO96/39999 | 12/1996 |

OTHER PUBLICATIONS

Parodi et al., "Transfemoral Intraluminal, Graft Implantation for Abdominal Aortic Aneurysms," Annals of Vascular Surgery volo. 5, No. 6, 1991, p. 491-499.

Criado et al., "Transluminal Recanalization, Angioplasty and Stenting in Endovascular Surgery: Techniques and Applications," from Greenhalgh, Vascular and Endovascular Surgical Techniques, 3$^{rd}$ Edition, 1994, pp. 49-70.

Marin et al., "Endoluminal Stented Graft Aorto-Bifemoral Reconstruction," from Greenhalgh, Vascular and Endovascular Surgical Techniques, 3.sup.rd Edition, 1994, pp. 100-104.

May et al., "Transluminal Placement of a Prosthetic Graft-Stent Device for Treatment of Subclavian Artery Aneurysm," Journal of Vascular Surgery, vol. 18, No. 6, Dec. 1993, pp. 1056-1059.

Chuter, T., "Bifurcated Endovascular Graft Insertion for Abdominal Aortic Aneurysm," from Greenhalgh, Vascular and Endovascular Surgical Techniques, 3.sup.rd Edition, 1994, pp. 92-99.

Parodi, J.C., "Transfemoral Intraluminal Graft Implantation for Abdominal Aortic Aneurysms," from Greenhalgh, Vascular and Endovascular Surgical Techniques, 3.sup.rd Edition, 1994, pp. 71-77.

Moore, W.S., "Transfemoral Endovascular Repair of Abdominal Aortic Aneurysm Using the Endovascular Graft System Device," from Greenhalgh, Vascular and Endovascular Surgical Techniques, 3.sup.rd Edition, 1994, pp. 78-91.

* cited by examiner ic
DELIVERY SYSTEM FOR MODULAR ENDOGRAFT WITH SUPERIOR ATTACHMENT SYSTEM This application is a continuation-in-part of U.S. application Ser. No. 10/222,728, filed Aug. 16, 2002.

BACKGROUND OF THE INVENTION

This invention relates to methods for delivering and deploying modular sections of an endovascular stent/graft for assembly thereof within the vasculature of a patient and specifically to a system for accomplishing the same.

It is well established that various fluid conducting body or corporeal lumens, such as veins and arteries, may deteriorate or suffer trauma so that repair is necessary. For example, various types of aneurysms or other deteriorative diseases may effect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft. Because a modular endovascular graft facilitates greater versatility of matching individual components to the dimensions of the patient's anatomy, the art has taught the use of modular endovascular grafts in order to minimize difficulties encountered with insertion of the devices into vasculature and sizing to the patient's vasculature.

Although the use of modular endovascular grafts minimize some of the difficulties, there are still drawbacks associated with the current methods. Drawbacks with current methods can be categorized in three ways; drawbacks associated with delivery and deployment of the individual endovascular graft components, drawbacks associated with the main body portion, and drawbacks associated with securing the limb portions to the main body portion.

Certain of the grafting apparatus for modular graft systems lack sufficient control of the deployment of self-expanding graft devices. While relying upon pusher assemblies to simply eject the graft devices from within a delivery sheath, precise positioning of the graft device is sometimes not accomplished. Such systems often lack subassemblies which facilitate the controlled delivery of modular, self-expanding graft devices which has been removed from a delivery sheath.

Additionally, certain of the available modular graft devices rely upon frictional engagement to ensure a graft-to-graft assembly of modular components. Other devices merely contemplate fully deploying a main graft component of a modular system and thereafter deploying subsequent graft components within a limited docking site, thereby resulting in a less adjustable assembly more concerned with precise assembly of graft components than compensating for a patient's anatomy.

There therefore exists a need for an endovascular graft delivery system that can be easily operated by a single technician without decreased reliability or additional risk to the patient. Additionally, a need exists for a delivery system that provides enhanced control of the delivery of self-expanding graft components of a modular design. Modular graft components including attachment systems that accomplish secure junctions are also needed as are graft support structures providing a reliable access to graft-to-graft junctions and enhanced ability to conform to patient anatomy.

The devices and methods of the present invention addresses these and other needs.

SUMMARY OF THE INVENTION

Briefly and in general terms, the present invention is embodied in delivery systems and methods which facilitate the deployment of graft devices within vasculature.

In one aspect, a delivery system is provided to accomplish implanting graft devices of a modular grafting apparatus at an interventional site. The delivery system includes a release subassembly which permits the precise positioning of self-expanding structure of a modular graft apparatus within vasculature. A proximal end portion of the delivery system is equipped with a support tube. The system also includes an inner catheter having a support tube and can when desired, include an inflatable balloon assembly.

In another aspect, the delivery system includes a superior capsule assembly operatively connected to a superior capsule grip. An inner catheter grip and main handle are also provided, each being longitudinally moveable with respect to each other and the capsule grip. An inner catheter lock is attached to an inferior end of the main handle and a collet snap assembly is configured on the superior capsule grip and inner catheter grip. Also provided is a release wire tab assembly which releasably mates with the main handle as well as flush chambers in fluid communication with flush ports.

Various graft components are contemplated. In one embodiment, a bifurcated graft component includes an attachment system with lumen penetrating members at a superior end portion and legs equipped with full-cell flat wire stents. In a second embodiment, the bifurcated graft component includes a superior attachment system and unsupported limbs. In a third embodiment, the bifurcated graft component includes an attachment system with lumen penetration members configured within a superior end of the device and one attachment system with lumen penetration members configured about an exterior of each leg portion. In a fourth embodiment of the bifurcated graft component, an anchoring system with alternating apices in combination with a plurality of interspersed V-shaped members is placed within a superior portion of the device and a self-expanding support system and an attachment system with lumen penetrating members is placed within each leg.

Various limb graft extensions are also contemplated. Certain of the limb graft extensions include attachment systems with lumen penetrating members configured within superior and inferior ends thereof. Other contemplated limb extensions include anchors without lumen penetrating members configured within or about an outer circumference of a limb extension component.

Methods associated with the in-situ assembly the components of the modular grafting systems are disclosed. In one particular method, the limb extensions are placed about the legs of a bifurcated graft. In another method, the limb extensions are placed within the limbs of a bifurcated graft component. A balloon catheter can be employed where desired to accomplish an effective junction assembly between component parts.

Other features and advantages of the present invention will become apparent from the following detailed description taken in conjunction with the accompanying drawings, which illustrate, by way of example, the principles of the invention.

DETAILED DESCRIPTION OF THE PREFERRED EMBODIMENTS

The present invention relates to systems and methods for accurately delivering and deploying the individual components of an endovascular graft at a treatment site within a patient's vasculature.

Figure 1:
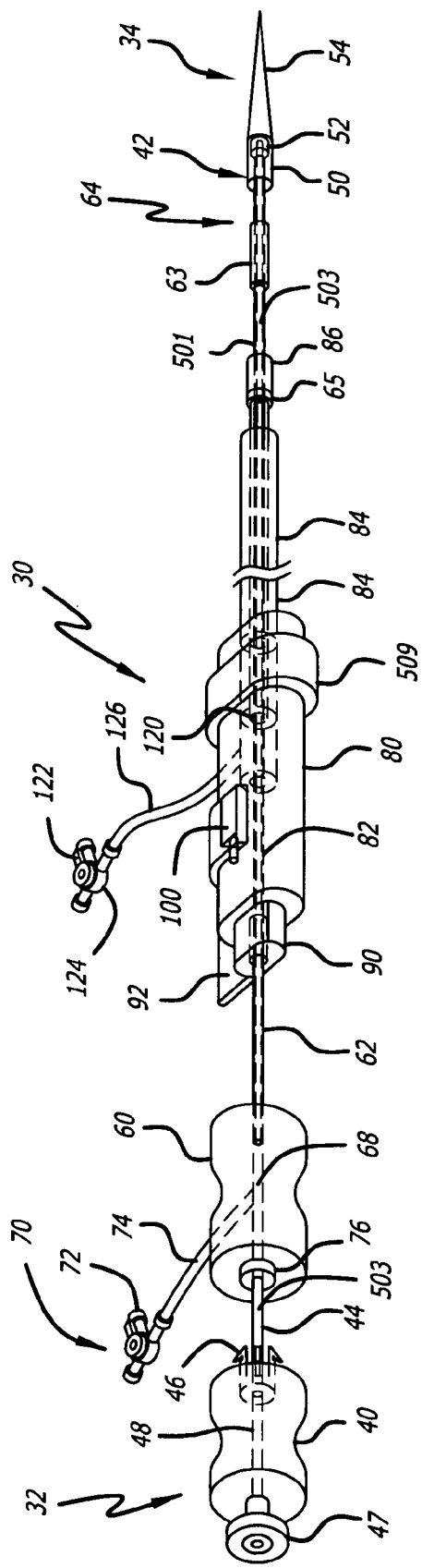
FIG. 1 is a perspective view, depicting a delivery system of the present invention.

With reference to FIG. 1, there is shown a delivery catheter 30. The delivery catheter includes an inferior end portion 32 and a superior end portion 34. The inferior end portion 32 includes a superior capsule grip 40 that is operatively associated with a superior capsule assembly 42 via an inner tube 503. The superior capsule grip 40 is designed for easy grasping by an operator and is longitudinally moveable relative to other components of the delivery catheter 30. The superior capsule grip 40 further includes a first male portion 46 of a collet snap assembly attached to a superior end thereof and an adaptor 47 attached to an inferior end. A lumen 48 sized to receive a guidewire extends through the adapter 47, capsule grip 40 and the first male part 46. It is contemplated that the superior capsule grip 40 remains exterior a patient's body during a procedure at an interventional site within the patient's vasculature.

Figure 2:
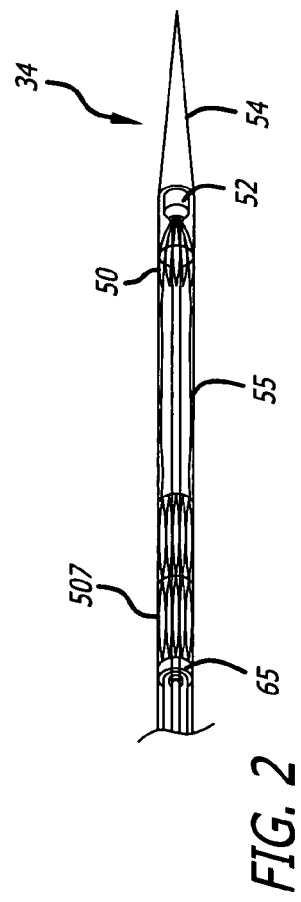
FIG. 2 is a partial cross-sectional view, depicting an enlarged superior end portion of the delivery system of FIG. 1 loaded with a graft component.

The superior capsule assembly (See also FIG. 2) includes a superior capsule 50, a capsule guard 52 and a nose cone 54. When in an assembled form, a portion of a graft 55 or other interventional device is tucked within an interior of the superior capsule 50, a terminal end thereof being placed adjacent or into engagement with the capsule guard 52. The nose cone 54 extends in a superior direction from the capsule 50 and has a tapered profile to thereby define a terminal end portion of the delivery catheter 30 suited for easy advancement within vasculature.

Figure 3:
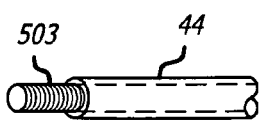
FIG. 3 is an enlarged perspective view, depicting a portion of a support tube of the delivery system of FIG. 1.

As shown in FIG. 3, the support tube 44 overlaps an inner tube 503. The inner tube 503 has a lumen sized to receive a guidewire or other medical device. The inner tube 503 extends from a connection to the superior capsule grip 40 through various other components of the delivery catheter 30 and is connected to the superior capsule assembly 42. Longitudinal forces applied to the superior capsule grip 40 are translated to the superior capsule assembly 42 via an inner tube 503 extending through the support tube 44 and through a lumen in the inner catheter 501. The support tube 44 embodies sufficient column strength and desired flexibility so that the longitudinal movement of the superior capsule grip 40 accomplishes predictable movement of the superior capsule assembly.

The delivery catheter can also include a second or balloon grip member 60 configured superior to the superior capsule grip 40. The second grip member 60 is also designed to fit comfortably in a hand of an operator and is contemplated to remain exterior a patient's body. The second grip member 60 is connected at a superior end to an inner catheter support tube 62 which extends in a superior direction toward the superior capsule assembly 42. A balloon or inflatable member 63 is formed along a superior end portion 64 of the inner catheter 501 and proximal the superior capsule assembly 42. The inner catheter support tube 62 extends over inner catheter 501 and prevents the inner catheter from buckling when second grip member 60 is translated. Middle tube 505 is equipped with an inferior retainer 65 in the form of a collar configured about the middle tube 505. The retainer 65 is positioned to aid in locating and retaining the inferior end of a graft or other medical device about the inner catheter 501.

Figure 4:
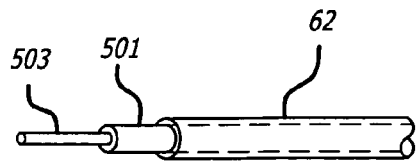
FIG. 4 is an enlarged perspective view, depicting a portion of an inner catheter support tube the delivery system of FIG. 1.

As shown in FIG. 4, the inner catheter support tube 62 overlaps an inner catheter 501 having at least one lumen. The lumen of the inner catheter 501 is sized to be commensurate with the lumen 68 extending through the second grip member 60 to thereby provide a continuous path from the inflation port to the inflatable member 63. Likewise, the lumen of the inner catheter support tube 62 is sized to slideably receive the support tube 44. The combination of the support tube 44 and inner catheter support tube 62 provide the delivery catheter 30 with desired pushability and flexibility for advancement within a patient's vasculature.

A lumen 68 extends through the second grip 60, the lumen being in fluid communication with an inflation port 70. The lumen is sized to receive the support tube 44 as well as provides a space for the transport of a medium such as air or liquids to the inflatable member 63. The inflation port 70 is equipped with a closeable adapter 72 and a tube 74 extending to the second grip 60 and being in fluid communication with the second grip lumen 68.

A second female portion 76 of a collet snap assembly is configured at an inferior end of the second grip 60. The second female portion 76 is designed to engage the first male portion 46 with an audible or sensory snap to thereby indicate an engagement between the two ports.

Still referring to FIG. 1, the delivery catheter 30 also includes a main handle 80 positioned superior to the second grip 60. A main handle lumen 82 extends the length of the main handle 80 and is sized to slideably receive the inner catheter support tube 62. Extending from a superior end of the main handle is a tubular inner sheath 84 that is sized to overlay the inferior end of the medical device mounted about a superior portion of the inner catheter 501. A terminal end 86 of the inner sheath overlays and retains the inferior end of the medical device between the inner sheath and the retainer 65. Outer sheath or jacket 507 (shown in FIG. 2 only) overlays medical device 55. Translational movement of the outer sheath slider (not shown) attached to the inferior end of the jacket 507 results in the longitudinal movement of the jacket 507 to expose and ultimately facilitate the deployment or release of a medical device 55 from the delivery catheter 30. Translational movement of the inner sheath slider 509 results in the longitudinal movement of the inner sheath and to expose and ultimately release the inferior end of the medical device.

Figure 5:
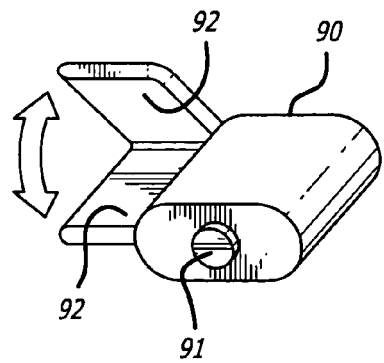
FIG. 5 is an enlarged perspective view, depicting a locking mechanism of the delivery system of FIG. 1.

A locking mechanism 90 (see also FIG. 5) is attached to an inferior end of the main handle 80. The locking mechanism includes an internal bore 91 sized to slideably receive the inner catheter support tube 62 and a rotatable arm 92 that causes the internal bore to decrease in size to thereby lock the main handle 80 to the inner catheter support tube 62.

Figure 6:
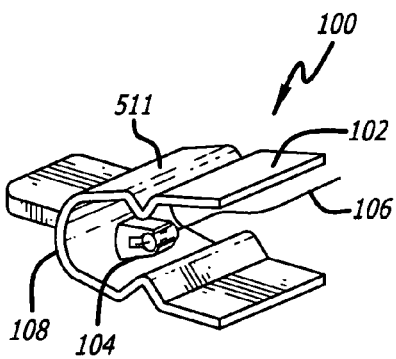
FIG. 6 is an enlarged perspective view, depicting a release wire tab assembly of the delivery system of FIG. 1.
Figure 7:
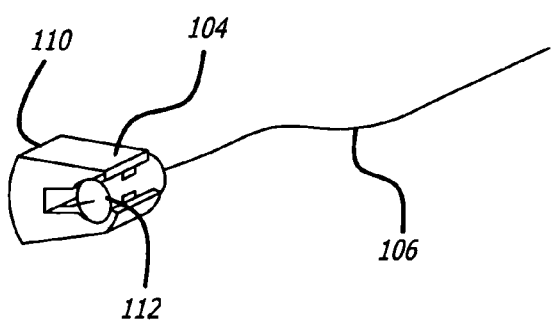
FIG. 7 is an enlarged perspective view, depicting a release wire female attachment of FIG. 6.

The main handle 80 further embodies a release wire snap assembly 100 that includes an outer member 102 and a release wire ferrule attachment 104 connected to a release wire 106 (See FIGS. 6 and 7). Although only one assembly is shown, it is contemplated that multiple snap assemblies can be provided. The outer member 511 includes arms 102 that snap fit about a portion of the main handle 80. An elbow 108 is configured to releasably receive the release wire ferrule attachment 104 and hold the same in place against the main handle 80 when the delivery system 30 is in its assembled form. The release wire ferrule attachment 104 includes a housing 110, an interior of which is sized to mate with a collar 112 attached to the release wire 106. The release wire in turn, extends longitudinally and is placed into engagement (not shown) with a medical device in a manner to maintain the medical device in or both of a compressed configuration and a stable longitudinal position within vasculature. Withdrawing the release wire can facilitate the expansion and release of the medical device from the delivery catheter 30 and within vasculature or other body lumen. For instance, the release wire 106 can be configured about a circumference of a medical device or configured through walls defining the medical device. For release wire operation reference U.S. Pat. No. 5,693,083 co-owned by Applicant and incorporated herein by reference in its entirety.

Figure 8:
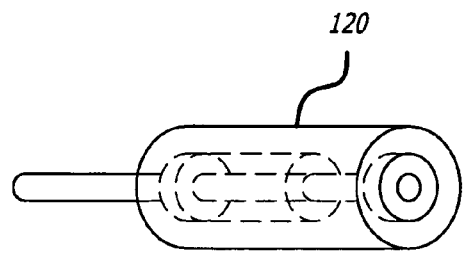
FIG. 8 is an enlarged perspective view, depicting a flush chamber of the delivery system of FIG. 1.

A flush chamber 120 (see also FIG. 8) can be configured within the main handle 80. The flush chamber 120 is placed in fluid communication with a flush port 122 and provides a mechanism for delivering a fluid within vasculature via the delivery catheter for the purpose of flushing an area of an interventional site. The flush port 122 can further include a closeable adapter 124 and a tube 126 connecting the closeable adapter 124 to the flush chamber 120.

Figure 9:
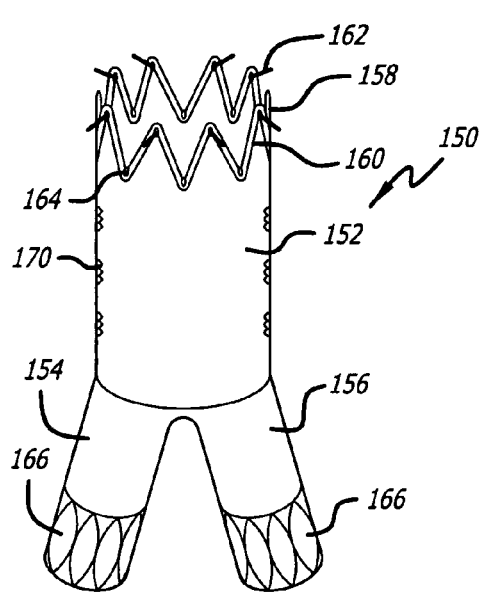
FIG. 9 is a perspective view, depicting one embodiment of a bifurcated graft component of a modular system.

Referring now to FIG. 9, a first embodiment of a graft or medical device 150 contemplated to be deployed within vasculature by the delivery catheter 30 can be a first component of a modular system or a sole implant device for use in an interventional procedure. Where it is desirable to build a modular system within vasculature, multiple delivery catheters 30 can be employed or multiple components can be configured within the delivery catheter 30. As shown, the graft device 150 can be bifurcated including a main body portion 152 and first and second leg portions 154, 156.

A superior end portion 158 of the graft device can include a self-expanding or balloon expandable stent device 160 which can be placed within an interior or about a circumference of the graft 150. The stent device 160 can be equipped with hooks or other lumen engaging members 162. The stent device can embody a plurality of alternating apices 164 connected to form a ring and that can be staggered longitudinally or not. The lumen engaging members 162 can be attached directly to the frame defining the stent device 160 or can embody a V-shaped member configured between the apices 164. Further, the apices 164 can include helical springs formed therein.

The legs 154, 156 of the graft device 150 also can be equipped with stent devices either of the form attached to the superior end portion 158 or stent devices having any other design including a single cell frame 166. Again, with this embodiment and each of the subsequently described embodiments, the stent devices can be placed about an exterior or an interior of a particular medical device. Moreover, although the graft device 150 is depicted as only including stent devices at terminal ends of the device, each of the medical devices can include stent devices extending a full length thereof. Moreover, radiopaque markers 170 can be placed strategically along the length or circumference of the described medical devices.

Figure 10:
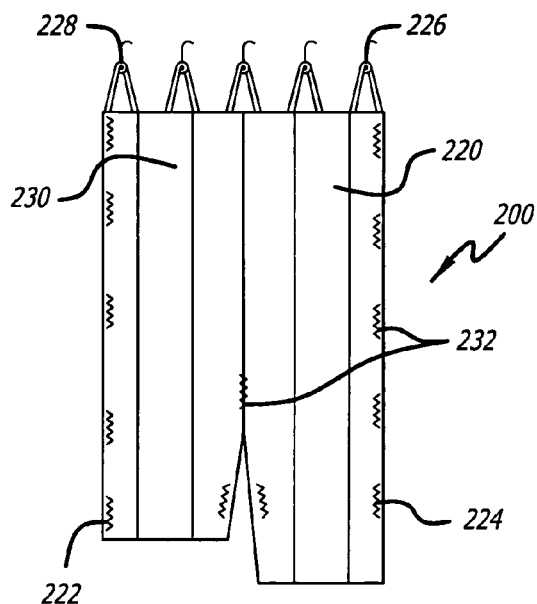
FIG. 10 is a side view, depicting a second embodiment of a bifurcated graft device of a modular grafting system.
Figure 11:
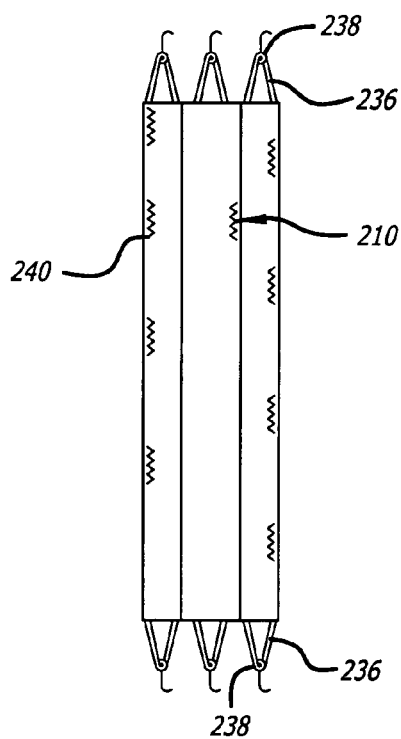
FIG. 11 is a side view, depicting one embodiment of a contralateral limb extension of a modular grafting system.
Figure 12:
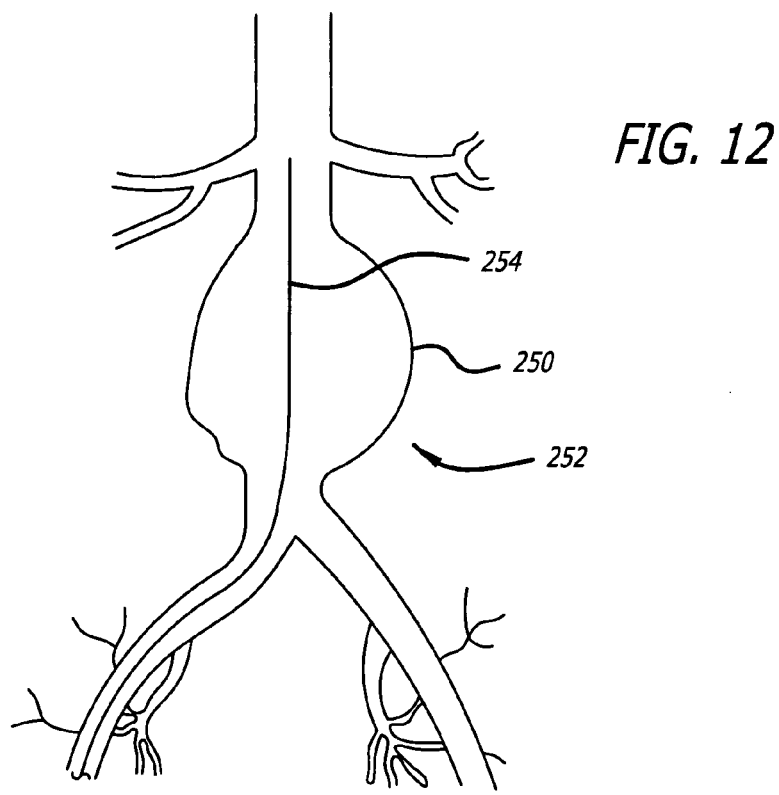
FIG. 12 is a partial cross-sectional view, depicting a first step in a process of repairing vasculature.
Figure 13:
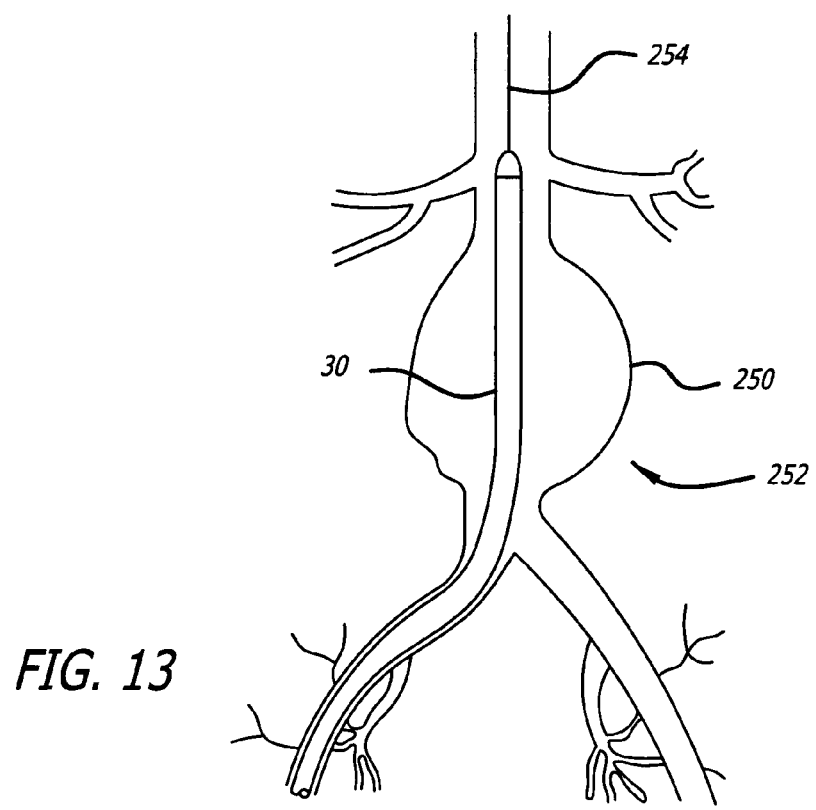
FIG. 13 is a partial cross-sectional view, depicting a second step in a repair process wherein the delivery system of FIG. 1 is placed at an interventional site within vasculature.
Figure 14:
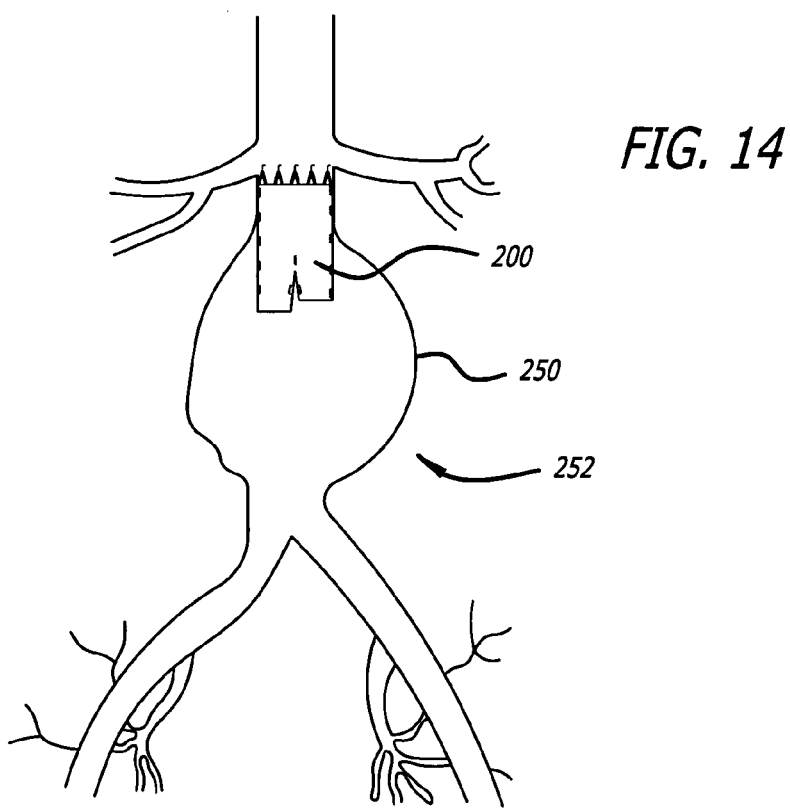
FIG. 14 is a partial cross-sectional view, depicting a second embodiment of the bifurcated graft component placed within vasculature.

Turning now to FIGS. 10 and 11, there is shown a second embodiment of a main body component 200 of a modular grafting device and a leg extension 210 that can be mated with the main body component 200 in vivo. The main body component 200 is bifurcated including a main trunk portion 220 and first and second leg portions 222, 224. In the embodiment shown, the main body component includes a stent device 226 with wall engaging members 228 attached to a superior end portion 230 thereof. Radiopaque markers 232 are again placed strategically along the device. Moreover, the legs 222, 224 can have varying lengths where one leg extends further than the other, although the legs can also be of equal length.

Whereas the main body portion 200 can be used as the sole device at an interventional site, in many cases it may be preferred to attach one or more of the leg extensions 210 to the main body 200. The leg extensions 200 can similarly be used to extend a superior portion of the main body 200. The leg extensions 210 include a stent device 236 connected to terminal ends thereof, although this structure can be fully stented as well. The stent devices can include hooks or lumen engaging members 238 suited for mating with the main body portion 200 or for penetrating vasculature. Radiopaque markers 240 are also included for remote visualization when the device is placed within a patient's body.

One contemplated use of the disclosed devices is for the repair of an aneurysm 250 formed in an aorta 252 of a patient (See FIGS. 12-15) though other areas of vasculature can be treated to address other conditions. In a first step of a method for repairing or treating an aneurysm 250, access to a patient's vasculature is attained via conventional techniques and a guidewire 254 is advanced within the vasculature and positioned transverse the aneurysm 250. A catheter 30 loaded with a medical device is advanced within the vasculature along the guidewire 254 and placed across the interventional site. After withdrawing the outer sheath 507 (See FIG. 2) and manipulating the various handles of the delivery catheter 30, the release wire or wires 106 (See FIG. 7) are pulled to release a graft device 200 from the catheter 30. The balloon or inflatable portion 63 of the delivery catheter can then be used to aid in implanting the superior portion 230 of the graft superior to the aneurysm 250.

Figure 15:
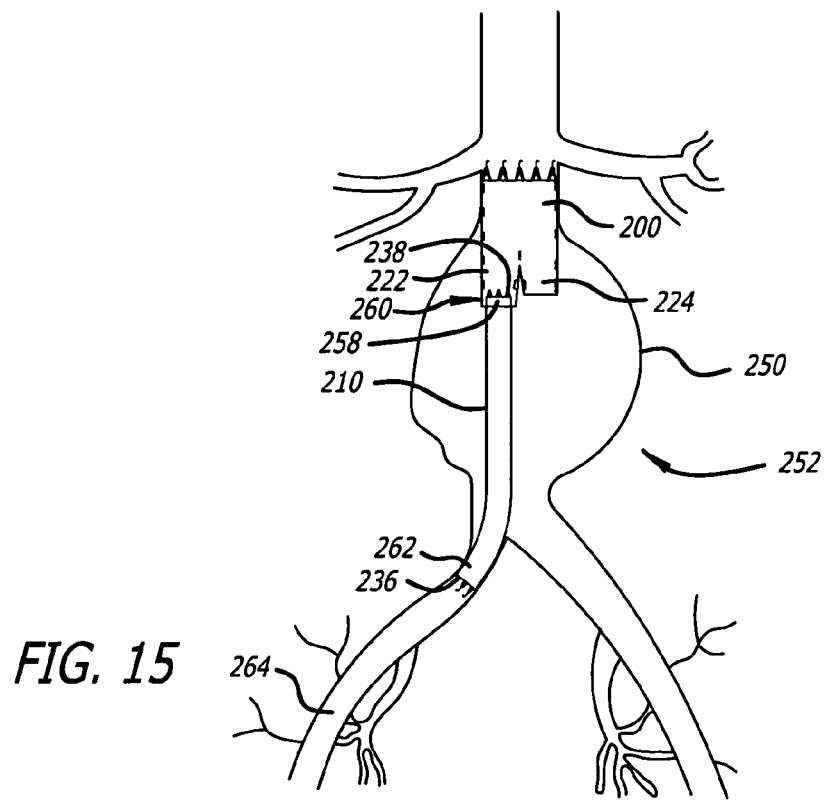
FIG. 15 is a partial cross-sectional view, depicting the ipsilateral limb extension of FIG. 12 attached to the bifurcated graft component of FIG. 15.

After implanting the main body portion 200 at the interventional site, the catheter 30 loaded with an extension component 210 or a separate catheter device, is employed to release and attach the extension component 210 to the main body component 200 (See FIG. 15). A superior end portion 238 of the extension component 210 is placed within a leg 222 of the main body component 200, the stent 236 and hooks 238 of the extension component accomplishing a secure connection between the two devices. An inferior end 262 of the extension component 210 is attached to an interior of a branch vessel 264.

Figure 16:
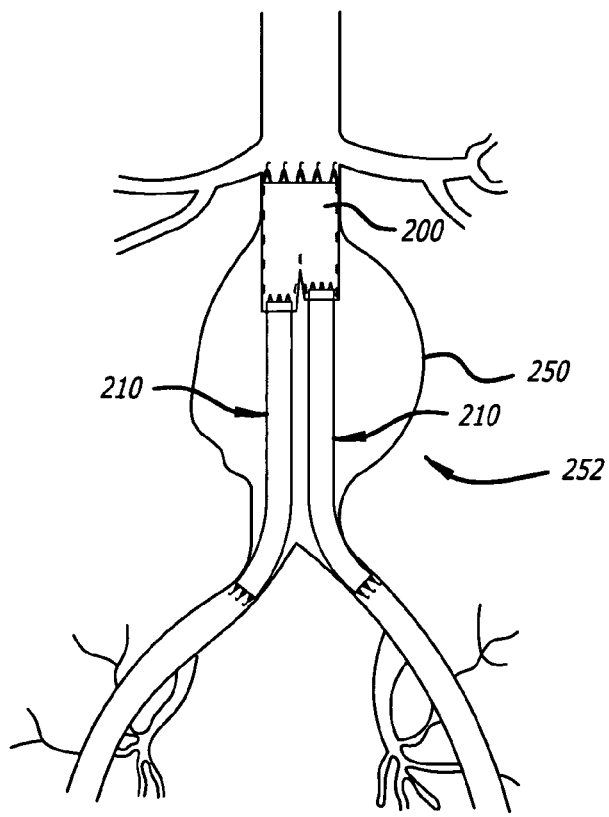
FIG. 16 is a partial cross-sectional view, depicting the contralateral limb extension of FIG. 11 attached to the assembly shown in FIG. 16.

A similar approach is taken to implant a second extension component 210 at the interventional site (See FIG. 16).

Figure 17:
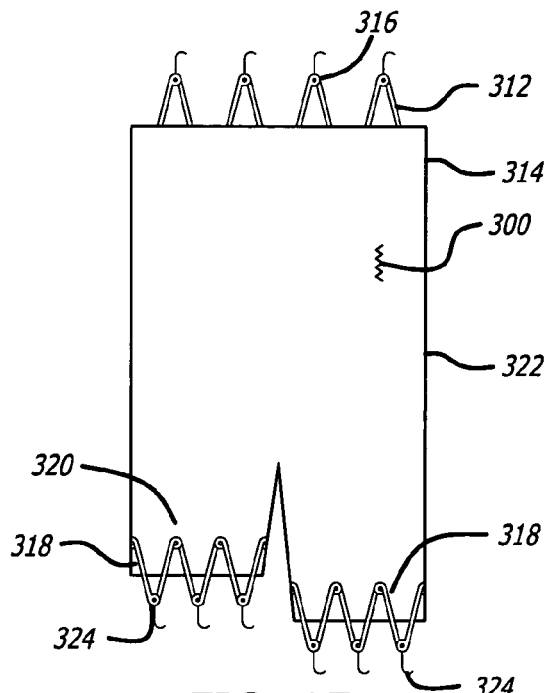
FIG. 17 is a side view, depicting a third embodiment of a bifurcated graft device of a modular grafting system.
Figure 18:
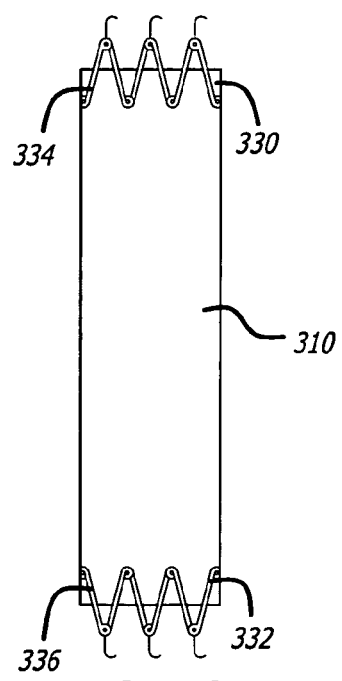
FIG. 18 is a side view, depicting another embodiment of a limb extension.
Figure 19:
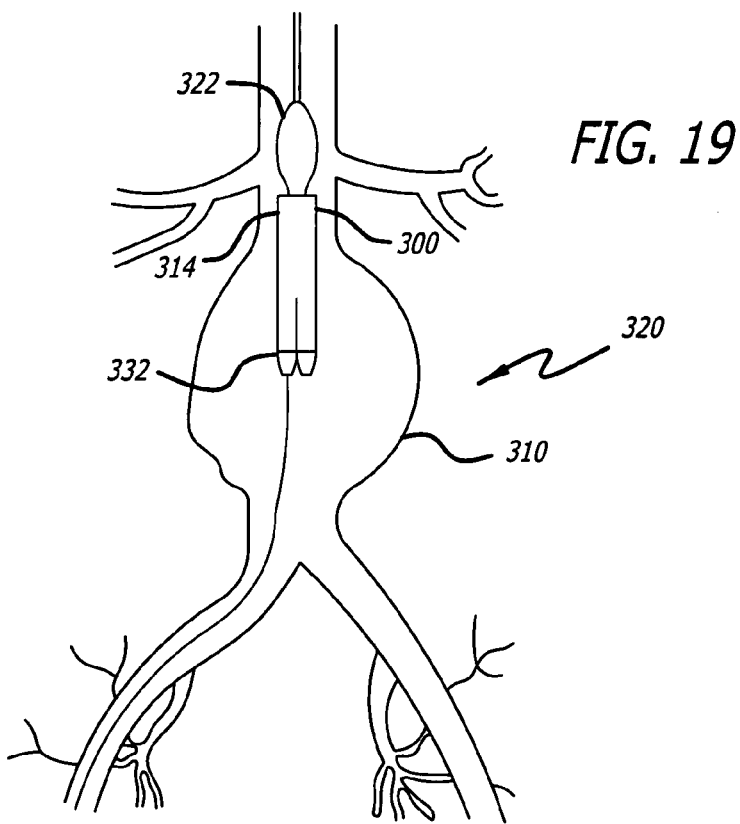
FIG. 19 is a partial cross-sectional view, depicting a third step of in the process of repairing vasculature.
Figure 20:
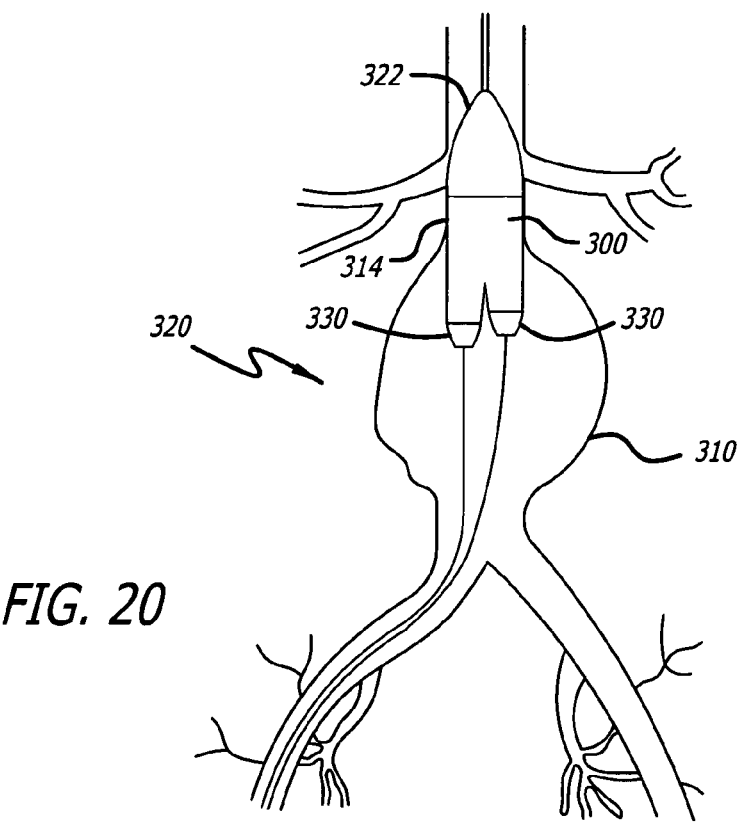
FIG. 20 is a partial cross-sectional view, depicting a fourth step of in the process of repairing vasculature.
Figure 21:
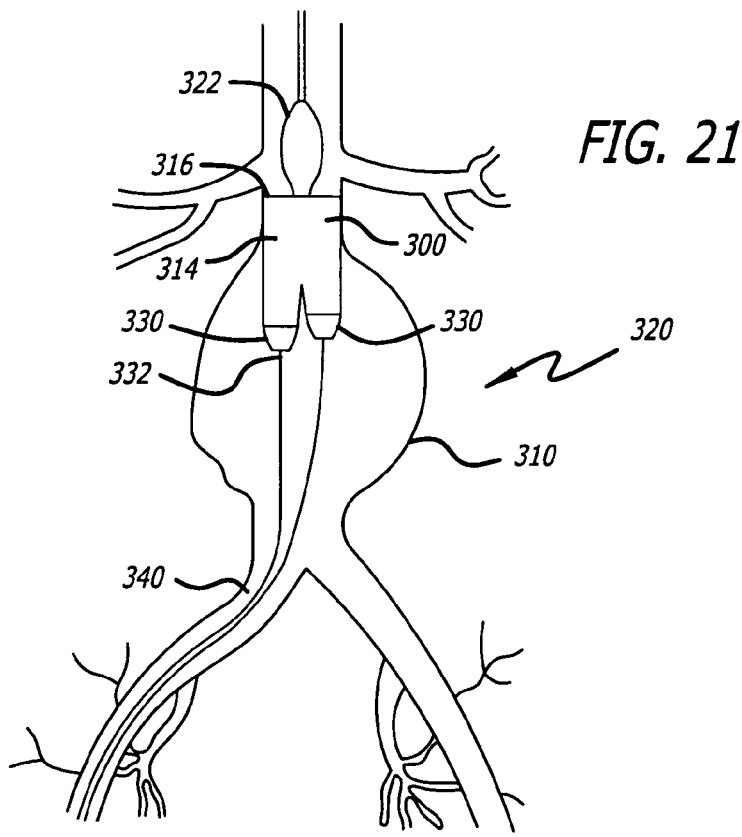
FIG. 21 is a partial cross-sectional view, depicting a fifth step of in the process of repairing vasculature.
Figure 22:
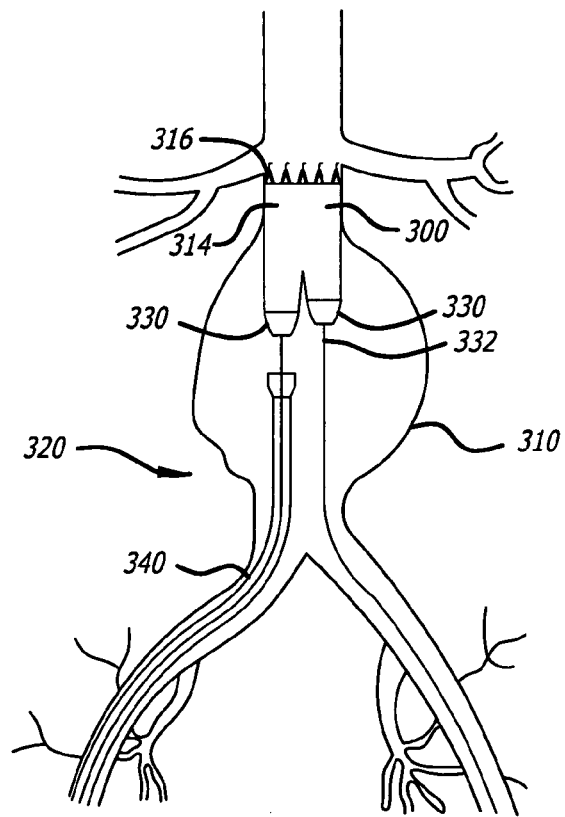
FIG. 22 is a partial cross-sectional view, depicting a sixth step of in the process of repairing vasculature.
Figure 23:
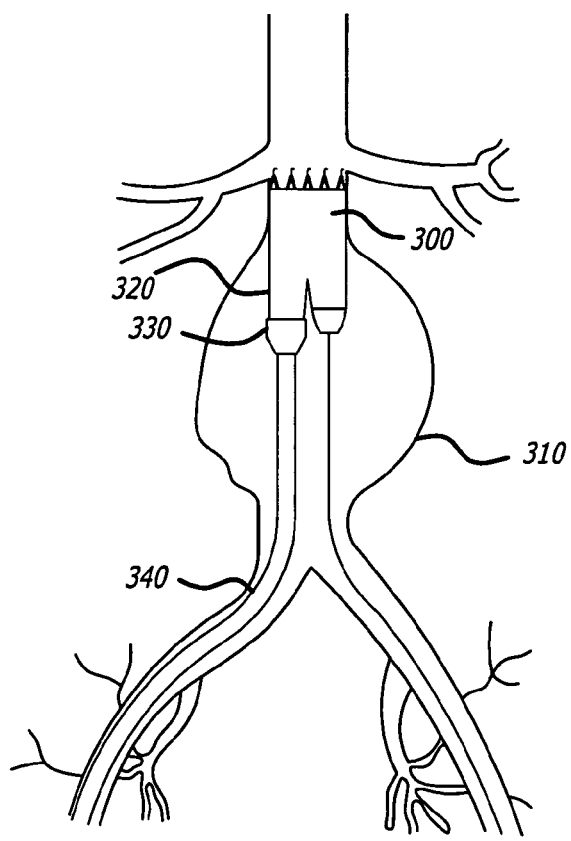
FIG. 23 is a partial cross-sectional view, depicting a seventh step of in the process of repairing vasculature.
Figure 24:
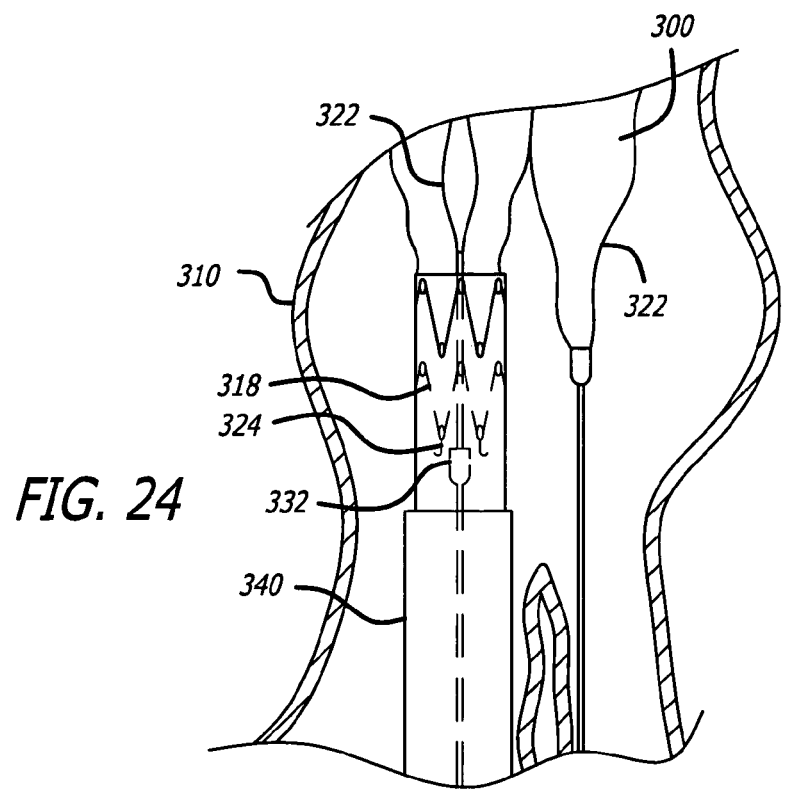
FIG. 24 is a partial and enlarged cross-sectional view, depicting a ninth step of in the process of repairing vasculature.
Figure 25:
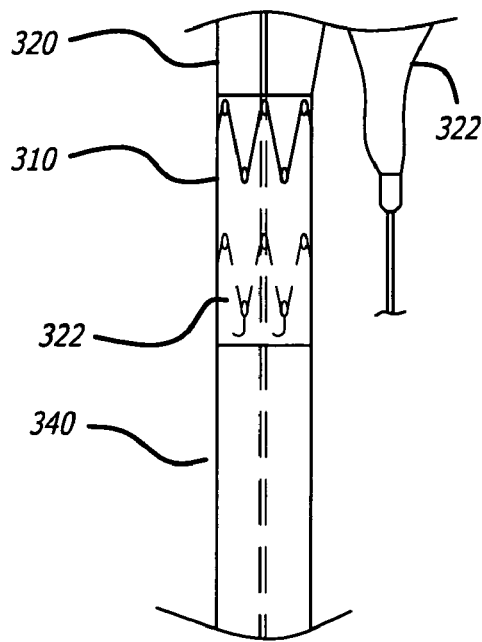
FIG. 25 is a partial and enlarged cross-sectional view, depicting a tenth step of in the process of repairing vasculature.
Figure 26:
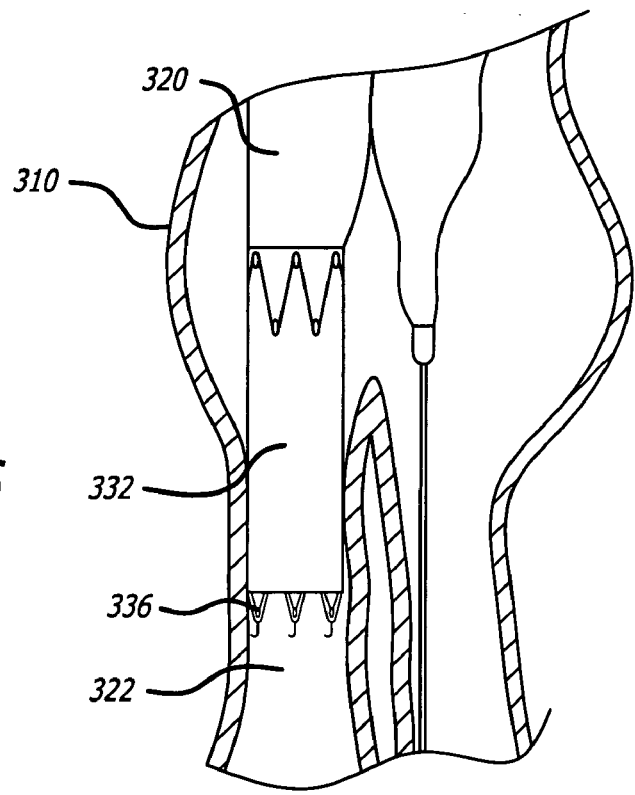
FIG. 26 is a partial and enlarged cross-sectional view, depicting an eleventh step of in the process of repairing vasculature.

Referring now to FIGS. 17 and 18, a third embodiment of a bifurcated graft device 300 and an associated extension component 310 is shown. The bifurcated graft device 300 includes a first stent device 312 attached to a superior end portion 314 thereof. The stent device 312 can be placed within an interior of the graft 300 and can further include hooks or lumen engaging members 316. Additional leg stent components 318 are attached about a periphery of limbs 320, 322 of the bifurcated graft device 300. The limbs 320, 322 can be of different length and although contemplated to be used as part of a modular grafting system intended to be assembled in situ, the bifurcated graft device 300 can also be used alone where appropriate. Additionally, the leg stent components 318 can include hooks 324 and again, the stents 318 can also be placed within an interior of the graft device 300. Moreover, as before, the stents can be self-expanding or balloon expandable.

The extension graft device 310 further includes a superior end portion 330 and an inferior end portion 332. A stent 334 is attached to the superior end portion 330 and a second stent 336 is attached to the inferior end portion 332, each placed about a periphery of the graft device. The first stent 334 lacks hooks but the second stent includes hooks or wall engaging members.

Turning now to FIGS. 19-26, an approach for delivery and implanting the graft devices of FIGS. 17 and 18 are depicted. Initially, access is gained to a patient's vasculature and the graft is placed via a delivery catheter 30 at an interventional site within vasculature. Although any suitable area of vasculature and malody can be treated, for purposes of illustration, the repairs of an aneurysm 310 in an aorta 320 is presented. After placing the graft device 300 within an aorta 310, an inflatable member or other expanding device 322 is expanded within an interior of the superior portion 314 of the graft device 300 to attach the graft within vasculature. The lumen engaging members 314 accomplish a secure anchor within the interventional site. While maintaining terminal end portions 330 of the legs of the graft device 300 in a compressed condition, the inflatable member 322 is deflated and removed from interaction from the superior portion 314.

A capsule or other restraining structure 332 is employed to maintain the terminal end portions 330 of the legs in a compressed condition. Extending inferiorly from the restraining means 332 are elongate members or wires which can provide a path to advance an extension component 310 to the interventional site. The extension component 310 is contemplated to be housed for advancement within vasculature in a delivery catheter 340 which can take any form including that previously described herein.

Through relative movement between the delivery catheter 340 and the extension component 310, the extension component 310 is released about an exterior of the leg 320 of the graft device 300, the leg being maintained in a compressed condition. Next, the retention means 322 is withdrawn from engagement with the terminal end 330 of the graft device 300 thereby allowing the stent 318 to self-expand or be expanded. The inflatable member 332 can then be withdrawn in an inferior direction and expanded to add in connecting the extension 310 to the main graft device 300. To aid in effecting a secure attachment, the hooks 324 are caused to extend through graft material of the extension component. The delivery catheter 340 is further withdrawn to deploy a full length of the extension graft 310. The catheter including the expandable member 322 can then be placed within an interior of the inferior portion 332 of the extension component 310 to thereby facilitate the attachment of the second stent 336 to vasculature. Although not shown, a similar approach can be taken to attach an extrusion member to the second leg 322. After the graft devices are implanted at the interventional site, the various catheters are removed from the patient's vasculature and the access to an interior of the patient's body is closed.

Figure 27:
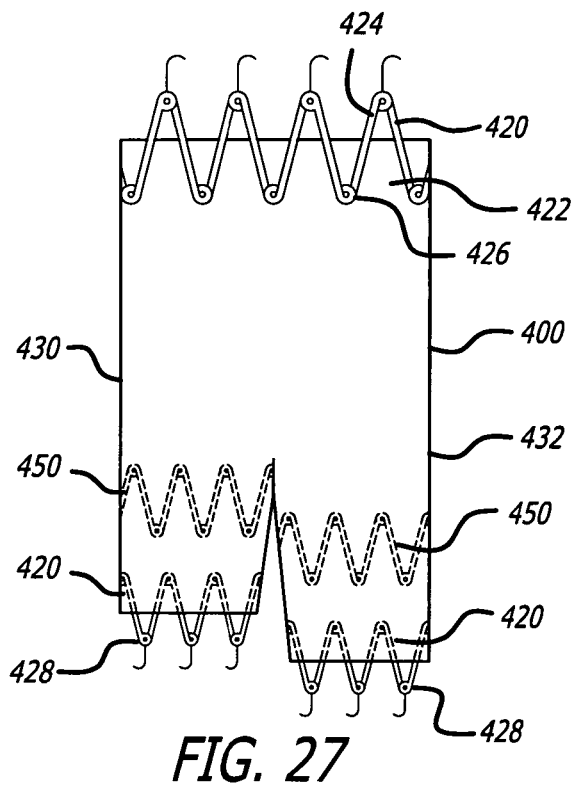
FIG. 27 is a side view, depicting a fourth embodiment of a bifurcated graft component of a modular grafting system.
Figure 28:
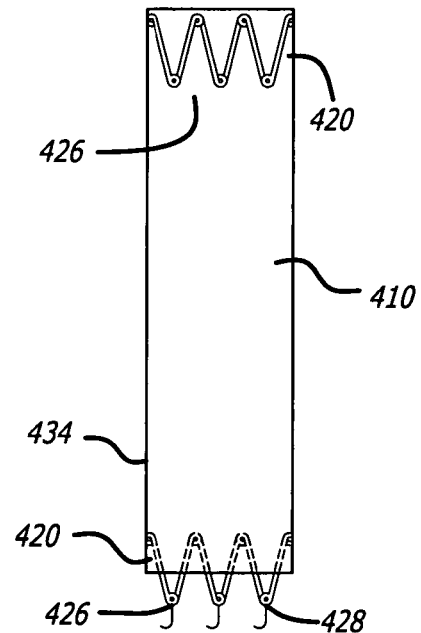
FIG. 28 is a side view, depicting yet another embodiment of a limb extension.

A fourth embodiment of a bifurcated graft 400 and an associated extension member 410 are shown in FIGS. 27 and 28. These devices can be deployed and implanted within vasculature as described above. Stent devices 420 having any of the previously described configurations can be placed within or about terminal end portions of the graft devices 400, 410. For example, a superior end portion 422 can include a stent device including V-shaped members with hooked ends 424 interspersed between various alternating apices of a stent device 420. Such members or alternatively, lumen engaging members 428 can be connected to the stent frames 420 placed within legs 430, 432 of the main graft component 400 or within an inferior end portion of the graft extension component 410. The various apices 426 of the stent devices 420 can as described above, can further include helical springs. Such stent structure 450 are also contemplated to be placed within or about other portions adjacent or remote from terminal ends of the graft devices 400, 410. The stent structures 450 can likewise include or lack hooks or other lumen penetration members and be placed at a single location or along an interior length of a graft device 400, 410.

It will be apparent from the foregoing that, while particular forms of the invention have been illustrated and described, various modifications can be made without departing from the spirit and scope of the invention. Accordingly, it is not intended that the invention be limited, except as by the appended claims and larger.

What is claimed is:

1. A system for treating vasculature, comprising:
    a first graft component, the first graft component including a self-expanding structure and an inferior end portion;
    a second graft component separate from the first graft component and configured to be delivered within vasculature separately from the first graft component; and
    a delivery catheter, the delivery catheter including a releasing mechanism, a sheath overlaying the releasing mechanism and the first graft component, and a restraining structure that maintains the inferior end portion of the first graft component in a reduced diameter, the releasing mechanism configured to maintain the self-expanding structure of the first graft component in a compressed configuration after the sheath is withdrawn exposing the self-expanding structures;
    wherein the second graft component has a superior end having an opening larger than the reduced diameter of the inferior end of the first graft component.

2. The system of claim 1, the first graft component further includes a superior end portion, the inferior end portion defining a first limb and a second limb.

3. The system of claim 2, the second graft component being configured to mate with one of the first and second limbs.

4. The system of claim 3, the second graft component being configured to anchor to an inside portion of one of the first and second limbs.

5. The system of claim 3, the second graft component being configured to anchor to an outer circumference of one of the first and second limbs.

6. The system of claim 3, the second graft component including an attachment system affixed to an external circumference of the second graft component.

7. The system of claim 6, the attachment system of the second graft component includes hooks.

8. The system of claim 1, the first graft component further including a plurality of self-expanding structure affixed thereto.

9. The system of claim 8, wherein at least one self-expanding structure is configured within an interior of the first graft component.

10. The system of claim 8, wherein at least one self-expanding structure is configured within an exterior of the first graft component.

11. The system of claim 8, at least one of the plurality of self-expanding structures include a lumen penetrating member.

12. The system of claim 11, wherein the lumen penetrating member is a hook.

13. The system of claim 11, at least one of the plurality of self-expanding structures further includes alternating apices and the lumen penetrating member is defined by a V-shaped member interspersed between the alternating apices.

14. The system of claim 8, wherein at least one of the plurality of self-expanding structures is placed in a medial portion of the first graft component.

15. The system of claim 14, wherein at least one of the plurality of self-expanding structures includes lumen penetrating members attached thereto.

16. The system of claim 15, wherein at least one of the plurality of self-expanding structures includes alternating apices between which is configured a V-shaped member which hooked terminal ends.

17. The system of claim 1, the second graft component including a plurality of self-expanding frames.

18. The system of claim 17, at least one of the self-expanding structures includes a lumen penetrating member.

19. The system of claim 18, at least one of the self-expanding structures lacking lumen penetrating members.

20. The system of claim 1, further comprising a third graft component.

21. The system of claim 1, the releasing mechanism further comprising a release wire tab assembly configured to releasably engage a handle of the delivery catheter.

22. The system of claim 1, the releasing mechanism further comprising at least one release wire configured to maintain self-expanding structure in a radially compressed condition.

23. The system of claim 1, further comprising a superior capsule assembly configured to receive a superior portion of the first graft component.

24. The system of claim 23, further comprising a support tube operatively connected to the superior capsule, and a superior capsule grip attached to an inferior portion of the support tube.

25. The system of claim 1, further comprising an inner catheter configured with an inflatable member.

26. The system of claim 1, further comprising an inner catheter grip attached to an inferior portion of the inner catheter.

* * * * *

UNITED STATES PATENT AND TRADEMARK OFFICE
CERTIFICATE OF CORRECTION

PATENT NO. : 7,591,843 B1  Page 1 of 1
APPLICATION NO. : 10/650477
DATED : September 22, 2009
INVENTOR(S) : Escano et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1599 days.

Signed and Sealed this

Twenty-first Day of September, 2010

David J. Kappos
*Director of the United States Patent and Trademark Office*